US012605266B1

(12) United States Patent
Stearns

(10) Patent No.: US 12,605,266 B1
(45) Date of Patent: Apr. 21, 2026

(54) SHEATH LACING ARRANGEMENT AND ASSOCIATED CARPOMETACARPAL (CMC) THUMB BRACE

(71) Applicant: Jeffrey B Stearns, Hopatcong, NJ (US)

(72) Inventor: Jeffrey B Stearns, Hopatcong, NJ (US)

(73) Assignee: Bullseye Brace, Inc., Hopatcong, NJ (US)

( * ) Notice: Subject to any disclaimer, the term of this patent is extended or adjusted under 35 U.S.C. 154(b) by 146 days.

(21) Appl. No.: 18/486,640

(22) Filed: Oct. 13, 2023

Related U.S. Application Data

(63) Continuation-in-part of application No. 17/842,480, filed on Jun. 16, 2022.

(60) Provisional application No. 63/252,284, filed on Oct. 5, 2021.

(51) Int. Cl.
    *A61F 5/058* (2006.01)
(52) U.S. Cl.
    CPC ................................ *A61F 5/05866* (2013.01)
(58) Field of Classification Search
    CPC .... A61F 5/05866; A61F 5/0118; A61F 5/013; A61F 2007/0038; A61F 2007/0036; A61F 5/0104; A61F 5/01; A61F 5/05858; A61F 5/05841; A61F 5/058; A61F 5/05; A61F 5/05875; A61F 5/10; A61F 2007/0037; A61F 2005/0186; A61F 5/0585; A61F 5/04; A61F 5/00; A41D 19/015; A41D 19/01582; A41D 19/01588
    See application file for complete search history.

(56) References Cited

U.S. PATENT DOCUMENTS 10,660,780 B1 * 5/2020 Ostergard ............. A61F 5/0104

* cited by examiner

*Primary Examiner* — Victoria Hicks Fisher
(74) *Attorney, Agent, or Firm* — QuickPatents; Kevin Prince

(57) ABSTRACT

A thumb brace for a person's hand includes a sheath for partially encircling a back of the hand, a thumb, and a front portion of a palm. The sheath includes two opposing lateral edges, a front edge, and a rear edge. A thumb retaining portion of the sheath has an open distal end adapted to receive the thumb therethrough. A retention mechanism is adapted to pull the two opposing lateral edges of the sheath towards each other to secure the sheath on to the hand. The thumb brace further includes a strap fixed at a first end thereof with the sheath, extending over the first web space of the hand, and fixable with an outside surface of the sheath. The strap and thumb retaining portion of the sheath together limit a range of motion of the thumb and the CMC joint.

14 Claims, 10 Drawing Sheets

SHEATH LACING ARRANGEMENT AND ASSOCIATED CARPOMETACARPAL (CMC) THUMB BRACE

CROSS-REFERENCE TO RELATED APPLICATIONS

This application is a Continuation-in-Part of U.S. Utility patent application Ser. No. 17/842,480, filed on Jun. 16, 2022, which itself claimed the benefit of U.S. Provisional Patent Application 63/252,284, filed on Oct. 5, 2021, both applications being incorporated herein by reference.

STATEMENT REGARDING FEDERALLY SPONSORED RESEARCH AND DEVELOPMENT

Not Applicable.

FIELD OF THE INVENTION

This invention relates to orthopedic brace devices, and more particularly to a thumb brace.

BACKGROUND

Thumb braces for limiting the range of motion of a person's thumb and stabilizing the carpometacarpal (CMC) joint are known in the art. Such prior art device, while effective in some ways, have the drawback of being uncomfortable for prolonged use, and often are made of materials that result in in discomfort due to sweat accumulation between the brace and the person's hand. Such prior art device are difficult to affix to one hand with the other hand, typically requiring the assistance of another person to put on.

Therefore, there is a need for a device that is comfortable to wear all day. Such a needed invention would be easy to don one-handedly, and would provide for the full range of motion for the person's other fingers. The present device helps relieve pain and inhibits subluxation of the CMC joint due to osteoarthritis by stabilizing the CMC joint with targeted compression by the strap and the retention mechanism, and by limiting the range-of-motion of, and inhibiting the collapse of, a distal end of the first metacarpal with the sheath 30 and the web space hook-and-loop fastener strip. Therapeutic warmth is provided to the arthritic hand while allowing breathability and a soft hand feel, allowing moisture to wick away from the hand for comfort. Further, such a needed device would be relatively simple to manufacture, and would be machine washable. The present invention accomplishes these objectives.

SUMMARY OF THE INVENTION

The present device is a thumb brace for a person's hand that includes a thumb, a plurality of fingers, a back, a palm, a first web space, and a carpometacarpal (CMC) joint. The thumb brace includes a sheath for partially encircling the back of the hand, the thumb, and a front portion of the palm. The sheath includes two opposing lateral edges, a front edge, and a rear edge. A thumb retaining portion of the sheath has an open distal end adapted to receive the thumb therethrough.

A retention mechanism is adapted to pull the two opposing lateral edges of the sheath towards each other to secure the sheath onto the hand. In preferred embodiments, the hook-side of each hook-and-loop fastener strip is fixed with one or more flexible cords that are fixable between the two opposing lateral edges of the sheath. Each cord is preferably fixed with the two opposing lateral edges of the sheath at grommets, disposed proximate each opposing lateral edge of the sheath. The retention mechanism allows the user to apply the thumb brace to one hand with the other hand.

The thumb brace further includes a strap fixed at a first end thereof with an interior surface of the sheath. The strap traverses a strap aperture formed in the sheath. The strap extends over the first web space of the hand, and a second end of the strap is fixable with an outside surface of the sheath. The strap further limits mobility of the CMC joint and acts as a "counter-force strap" that helps control the range-of-motion of the thumb and prevent the collapse of the distal end of the first metacarpal of the thumb which occurs over time if thumb arthritis is left untreated.

The present invention is comfortable to wear all day. The present device is easy to don one-handedly, and provides for the full range of motion for the person's other fingers. The thumb brace of the present invention provides the ability of the user to make sure the brace is located properly. Further, present invention is relatively simple to manufacture, and is machine washable. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
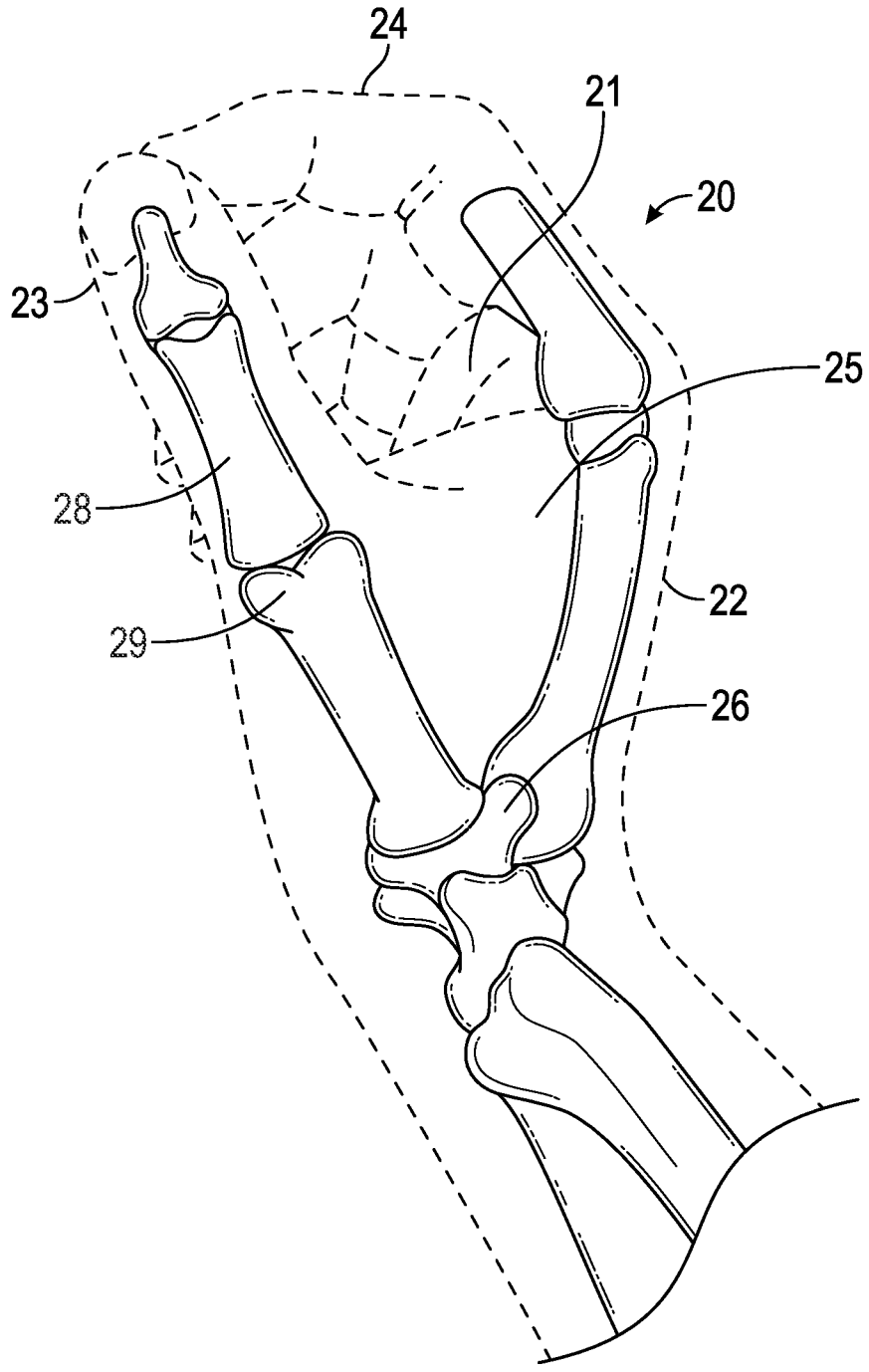
FIG. 1 is a diagram of a human hand showing bones and joints thereof, particularly a carpometacarpal (CMC) joint.
Figure 2:
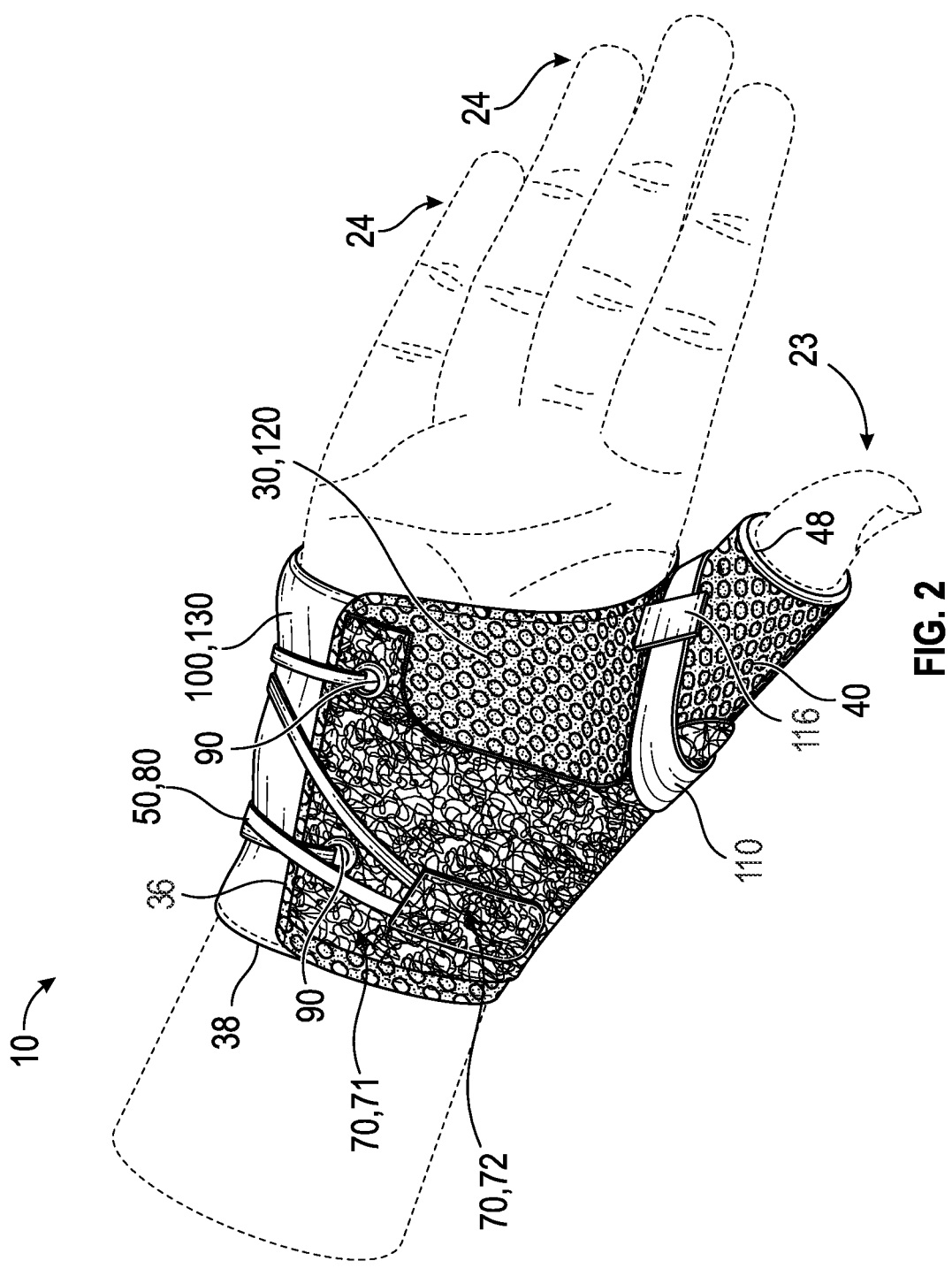
FIG. 2 is a top perspective view of the invention, shown as worn on the human hand and in a fastened configuration.

FIGS. 1-2 illustrate a thumb brace 10 for a human hand 20 that includes a thumb 23 having a first metacarpal 28, a plurality of fingers 24, a back 22, a palm 21, a first web space 25, an MCP joint 29, and a carpometacarpal (CMC) joint 26.

Figure 3:
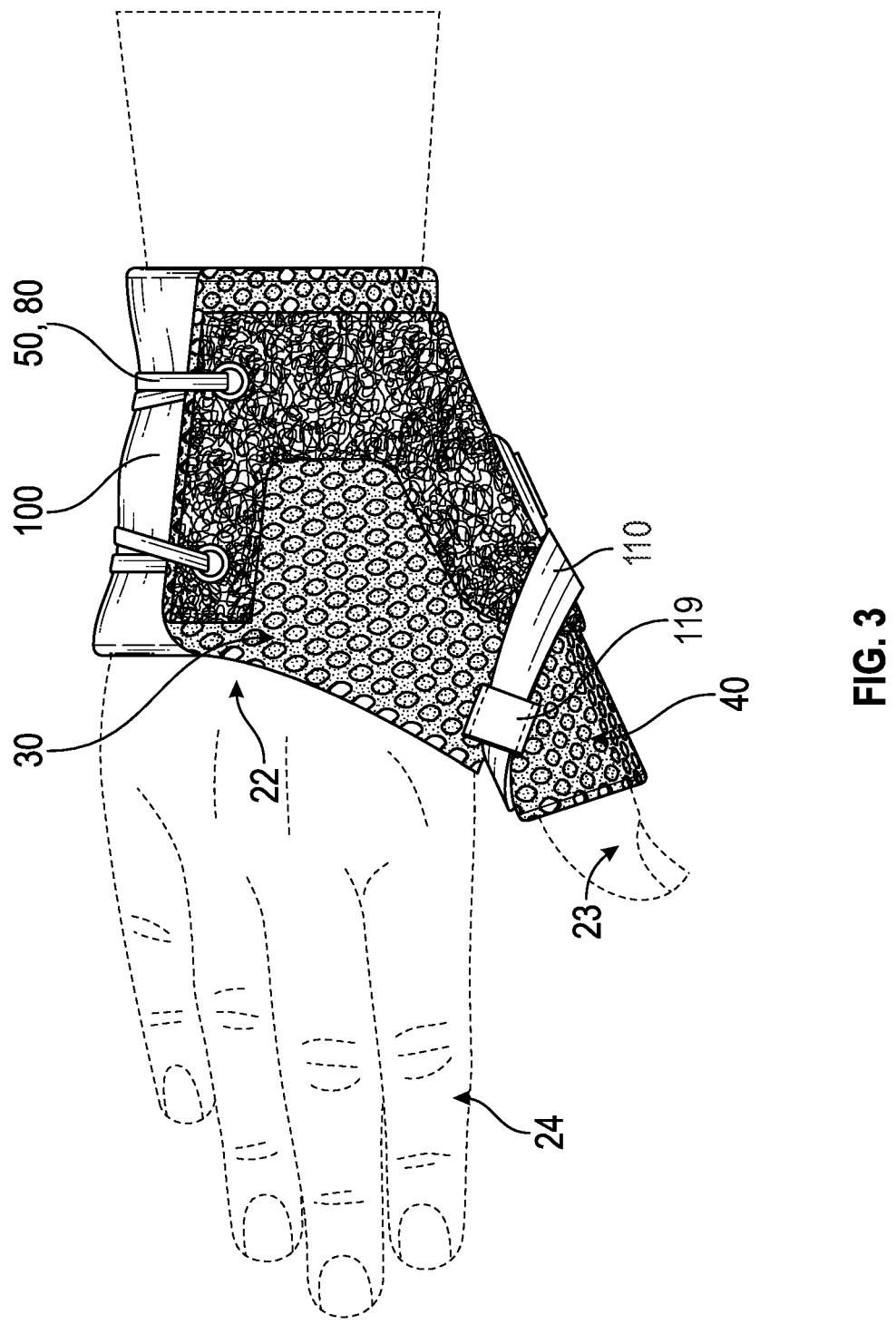
FIG. 3 is a top plan view thereof.
Figure 4:
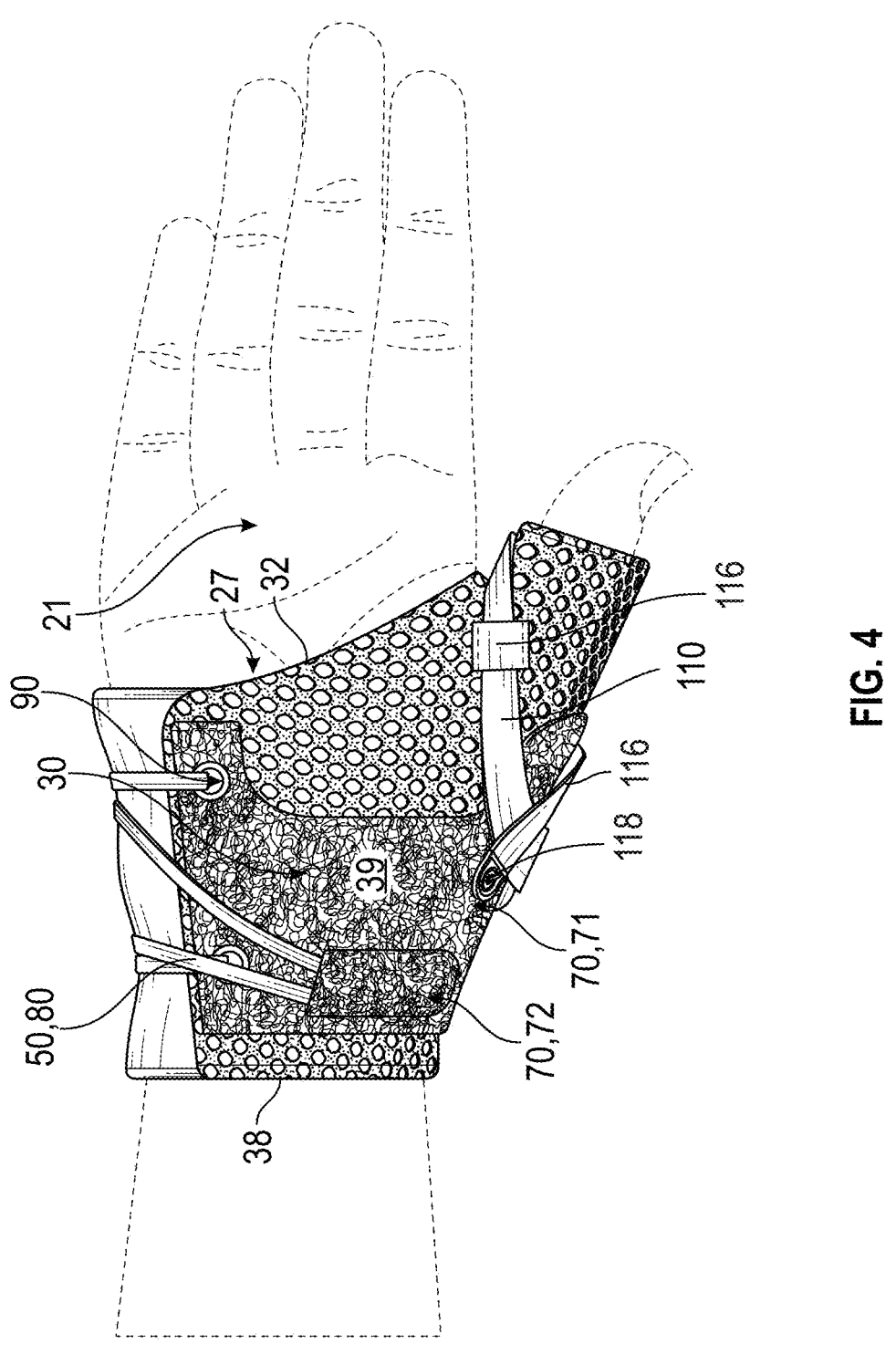
FIG. 4 is a bottom plan view thereof.
Figure 5:
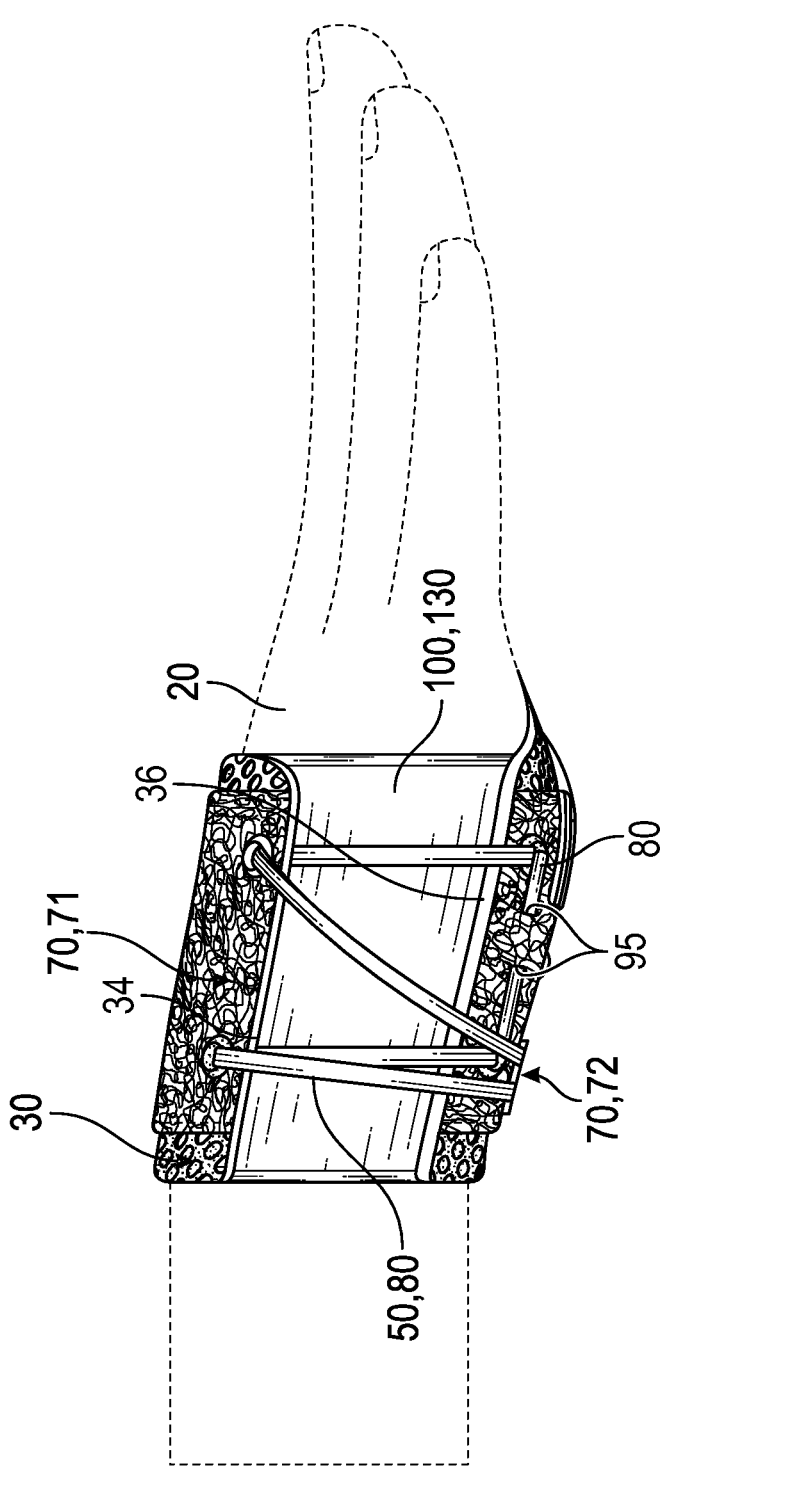
FIG. 5 is a left-side elevational view thereof.
Figure 6:
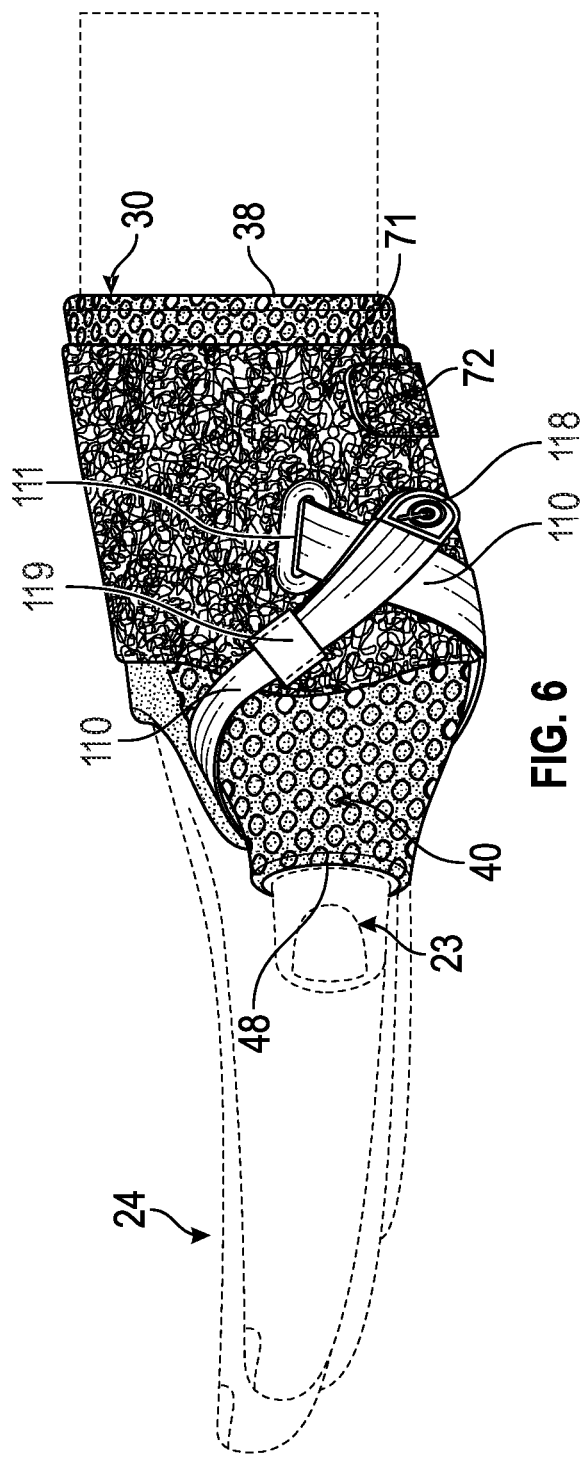
FIG. 6 is a right-side elevational view thereof.
Figure 7:
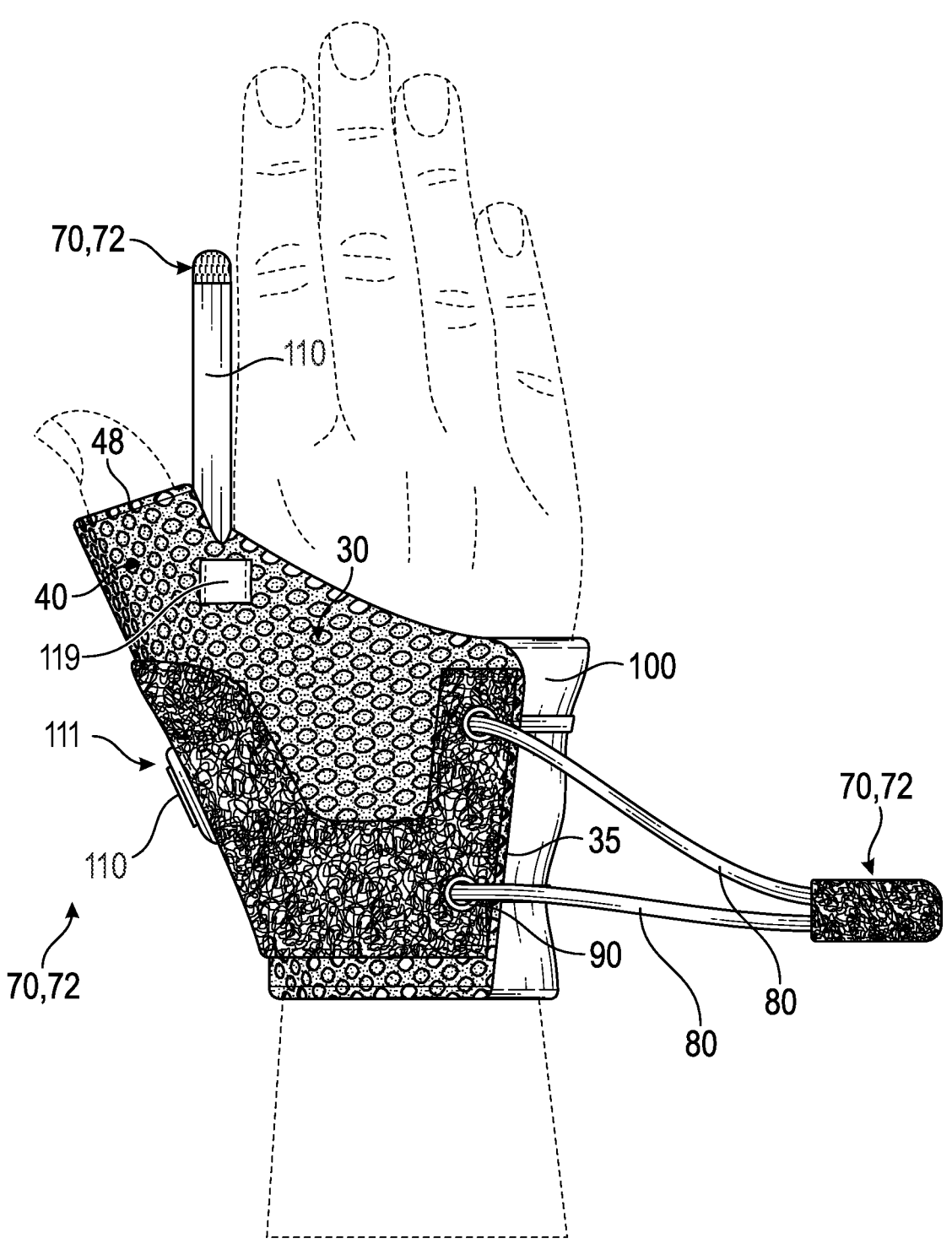
FIG. 7 is a top plan view thereof, illustrated in an unfastened position.
Figure 8:
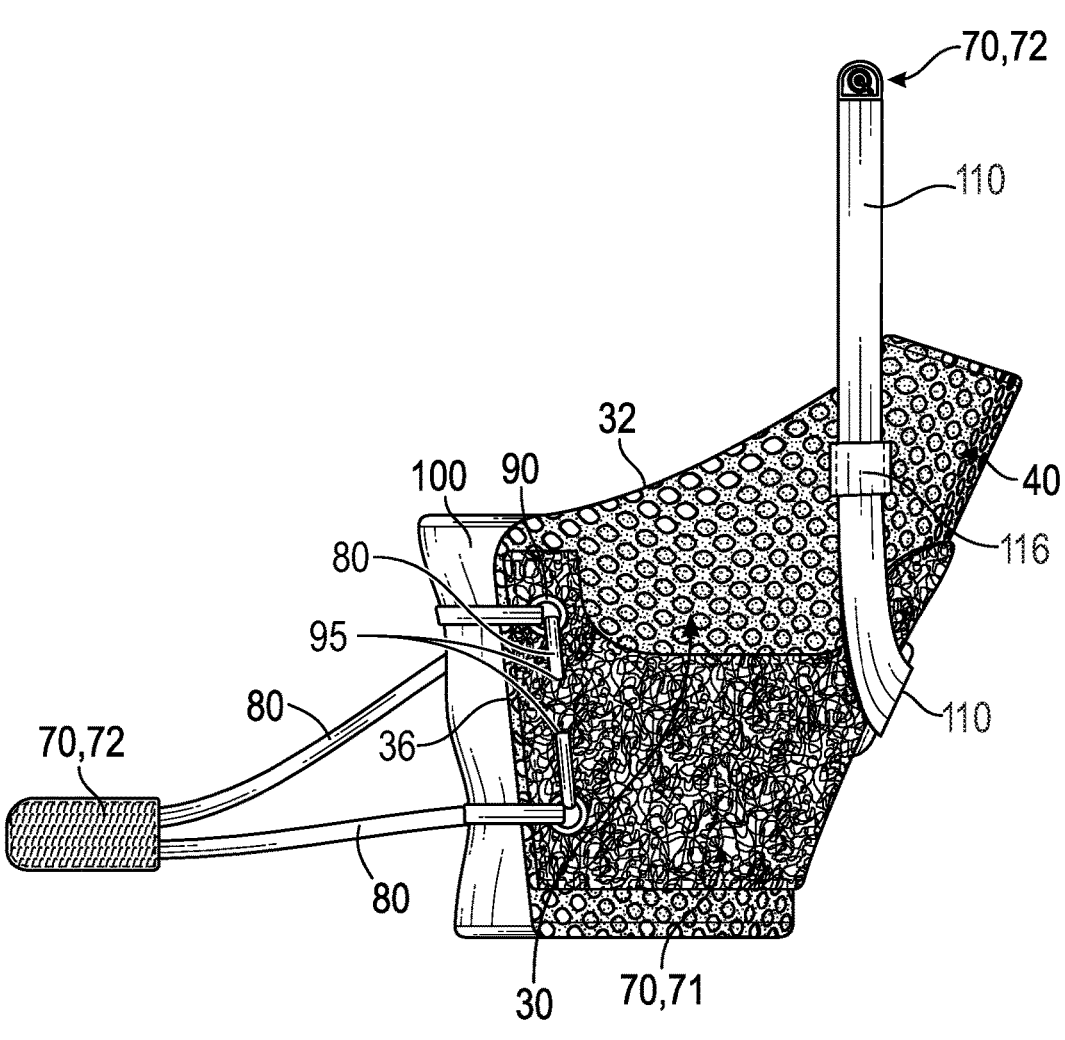
FIG. 8 is a bottom plan view of FIG. 7.

The thumb brace 10 includes a sheath 30 for partially encircling the back 22 of the hand 20 (FIG. 3), the thumb 23, and a front portion 27 of the palm 21 (FIG. 4). The sheath 30 includes two opposing lateral edges 35 (FIG. 5), a front edge 32 (FIGS. 4 and 8), and a rear edge 38. A thumb retaining portion 40 of the sheath 30 has an open distal end 48 adapted to receive the thumb 23 therethrough (FIGS. 6 and 7). The sheath 30 preferably includes a moisture wicking spacer fabric material 120. The figures illustrate the thumb brace 10 for the person's right hand 20, it being understood that the thumb brace 10 for the person's left's hand is a mirror image thereof.

A retention mechanism 50 (FIG. 5) is adapted to pull the two opposing lateral edges 35 of the sheath 30 towards each other to secure the sheath 30 on to the hand 20. In some embodiments, the retention mechanism 50 includes one or more hook-and-loop fastener strips 70, a loop-side of each hook-and-loop fastener strip 70 being fixed with the sheath 30, and a hook-side 72 of each hook-and-loop fastener strip 70 being removable fixable between the two opposing lateral edges 35 of the sheath 30. The retention mechanism 50 allows the user to apply the thumb brace to the hand 20 with the other hand.

In preferred embodiments, the hook-side 72 of each hook-and-loop fastener strip 70 is fixed with one or more flexible cords 80 that are fixable between the two opposing lateral edges 35 of the sheath 30. Each cord 80 is preferably fixed with the two opposing lateral edges 35 of the sheath 30 at grommets 90, disposed proximate each opposing lateral edge 35 of the sheath 30.

Other embodiments of the retention mechanism 50 may include elastic bands (not shown), elastic fabric (not shown), or other means of urging each of the opposing lateral edges 35 of the sheath 30 together.

In some embodiments, a flexible fabric web 100 is disposed between each of the two opposing lateral edges 35 of the sheath 30. As such, the cords 80 are inhibited from pressing into the person's hand 20. Such a flexible fabric web 100 preferably includes a faux suede cloth material 130, or the like.

Figure 9:
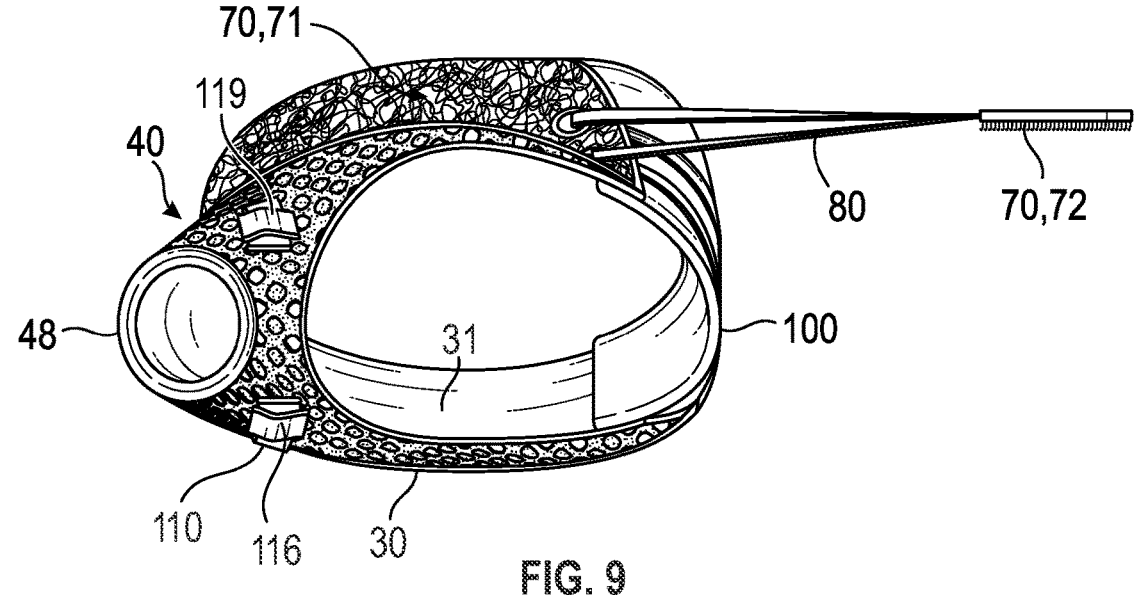
FIG. 9 is a front elevational view thereof.

The thumb brace 10 further includes a strap 110 fixed at a first end 112 thereof with an interior surface 31 (FIG. 9) of the sheath 30. The strap 110 traverses a strap aperture 111 formed in the sheath 30. The strap 110 extends over the first web space 25 of the hand 20, and a second end 118 of the strap 110 is fixable with an outside surface 39 of the sheath 30. The strap 110 further limits mobility of the CMC joint 26 and acts as a "counter-force strap" that helps control the range-of-motion of the thumb 23 and prevent the collapse of the distal end of the first metacarpal 28 of the thumb 23 which occurs over time if thumb arthritis is left untreated. One or more strap loops 116, 119 may be fixed with the thumb retaining portion 40 and adapted to receive the strap 110 therethrough.

Figure 10:
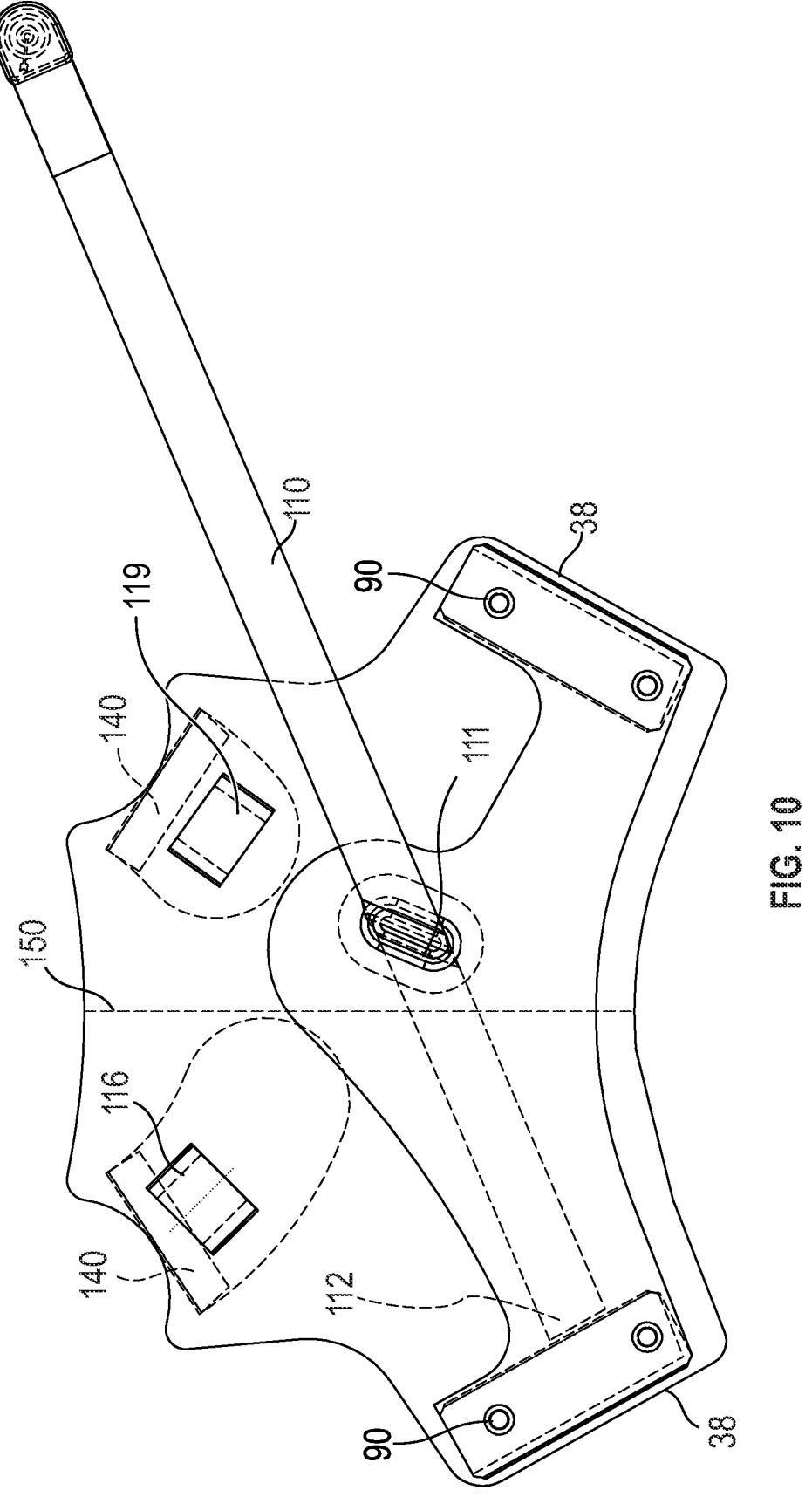
FIG. 10 is a pattern for the sheath before folding.

FIG. 10 illustrates a pattern for the sheath 30 before folding along a fold line 150 and sewing. The sheath 30 may be folded several times proximate the rear edge 38 thereof to reinforce the grommets 90. The first end 112 of the strap 110 preferably is fixed with the interior surface 31 of the sheath 30 proximate the rear edge 38 of the sheath 30 (FIG. 10). The strap 110 traverses the palm 21 and passes over the CMC joint 26, emerging from and pulling back against the strap aperture 111 which may include a silicone, flexible ring. The strap 110 wraps around the base of the thumb 23 and crisscrosses back over the CMC joint 26, thereby passing over the CMC joint 26 three times to provide stability to the CMC joint 26, to limit both flexion and extension of the $1^{st}$ metacarpal, and to help resist collapse of the MCP joint 29 (FIG. 1).

Figure 11:
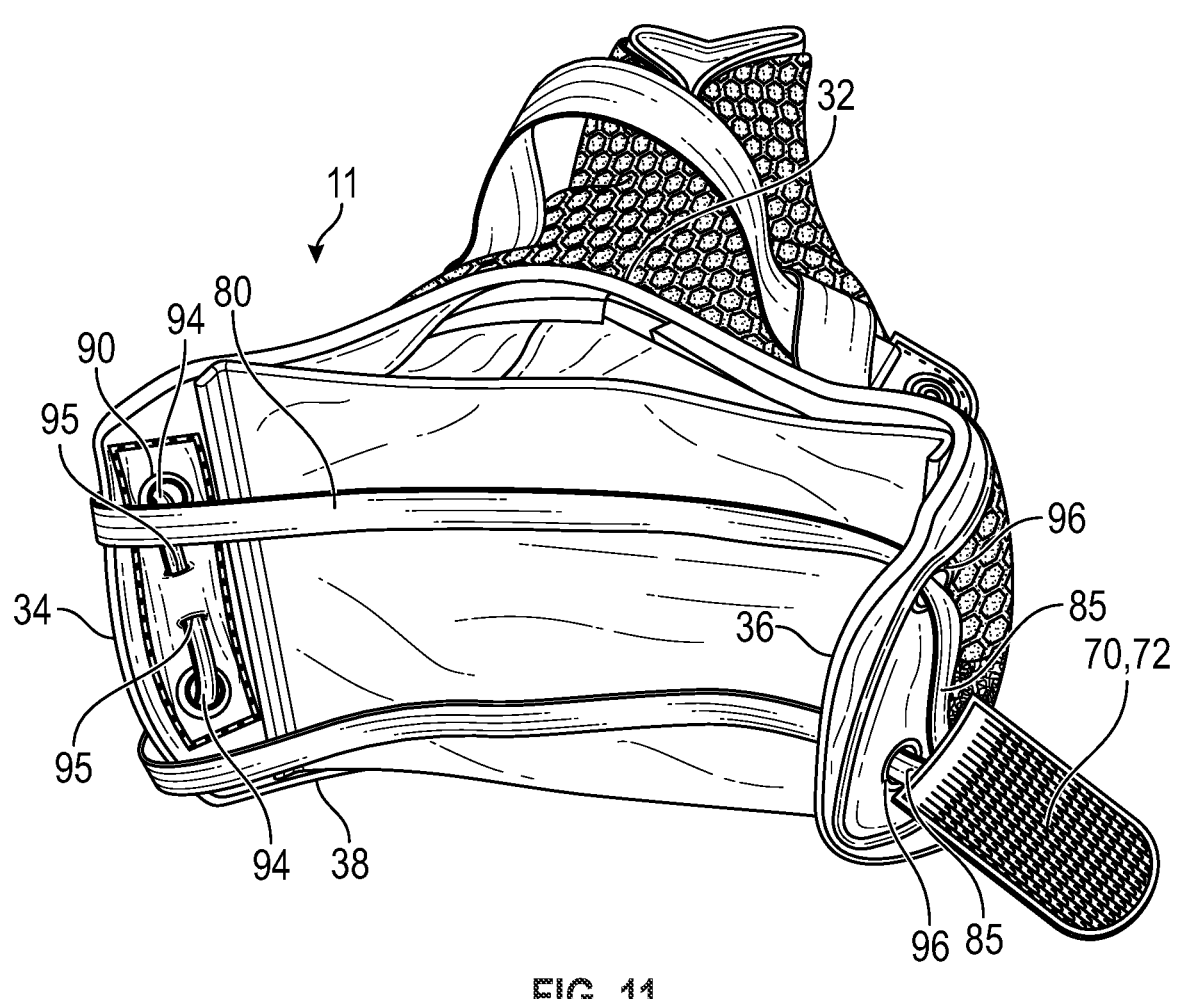
FIG. 11 is a side perspective view showing a lacing arrangement of the invention.

FIG. 11 illustrates a lacing arrangement 11 for an appendage of the person 20, such as the person's thumb 23, comprising at least one pair of first lace apertures 94 traversing the sheath 30 proximate a first lateral edge 34 of the sheath 30. A pair of second lace apertures 96 traverse the sheath 30 proximate a second lateral edge 36 of the sheath 30. A pair of slits 95 traverse the sheath 30 proximate the first lateral edge 34 and between each of the at least one pair of first lace apertures 94.

In such an embodiment, at least one of the cords 80 has two opposing ends 85 and is threaded through one of the second lace apertures 96 from the outside surface 39 to the interior surface 31, around the first lateral edge 34 of the sheath 30 and through one of the first lace apertures 94 from the outside surface 39 to the interior surface 31, through one of the slits 95 from the interior surface 31 to the outside surface 39, through an other of the slits 95 from the outside surface 39 to the interior surface 31, through an other of the first lace apertures 94 from the interior surface 31 to the outside surface 39, around the first lateral edge 34 of the sheath 30 and back through an other of the second lace apertures 96. The two opposing ends 85 of the at least one cord 80 fixed together with an attachment mechanism, such as one or more of the hook-and-loop fastener strips 70. As such, the at least one cord 80 can be pulled from the outside surface 39 between the two slits 95 to adjust the length of the cord 80.

In preferred embodiments, one or more pockets 140 are fixed with the interior surface 31 of the sheath 30 proximate the first web space 25 of the hand 20. Each pocket 140 is adapted for receiving an insert (not shown) that wraps around the first web space 25 of the hand 20 when the thumb brace 10 is worn on the hand 20. The insert further limits the range of motion of the first metacarpal 28 and stabilizes the CMC joint 26. The insert is preferably a resilient or flexible elastomeric or plastic pad.

While a particular form of the invention has been illustrated and described, it will be apparent that various modifications can be made without departing from the spirit and scope of the invention. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A sheath for securing about an appendage of a person, comprising:

the sheath having an outside surface, an interior surface, a front edge, a rear edge, a first lateral edge and a second lateral edge; and a lacing arrangement comprising:

at least one pair of first lace apertures traversing the sheath proximate the first lateral edge of the sheath;

at least one pair of second lace apertures traversing the sheath proximate the second lateral edge of the sheath;

a pair of slits traversing the sheath proximate the first lateral edge and between each of the at least one pair of first lace apertures; and at least one cord having two opposing ends and threaded through one of the at least one pair of second lace apertures from the outside surface to the interior surface, around the first lateral edge of the sheath and through one of the at least one pair of first lace apertures from the outside surface to the interior surface, through one of the pair of slits from the interior surface to the outside surface, through an other of the pair of slits from the outside surface to the interior surface, through an other of the at least one pair of first lace apertures from the interior surface to the outside surface, around the first lateral edge of the sheath and back through an other of the at least one pair of second lace apertures, the two opposing ends of the at least one cord fixed together with one or more hook-and-loop fastener strips;

whereby the at least one cord may be pulled from the outside surface between the pair of slits to adjust a length of the at least one cord, the sheath secured about the person's appendage, the one or more hook-and-loop fastener strips pulled tight and secured to the sheath with an attachment mechanism, the sheath thereby being secured to the person's appendage.

2. The sheath of claim 1 wherein the attachment mechanism of the one or more hook-and-loop fastener strips include a hook-and-loop fastening material for matting with corresponding hook-and-loop fastening material fixed with the sheath.

3. The sheath of claim 1 wherein the at least one cord is an elastic cord.

4. The sheath of claim 1 wherein the sheath is configured as a thumb brace adapted to be worn to partially encircle a back of a hand, thumb, and a front portion of a palm of the hand, the sheath further including a thumb retaining portion having an open distal end adapted to receive the thumb therethrough;

a strap fixed at a first end with the interior surface of the sheath, traversing a strap aperture formed in the sheath, the strap adapted to extend over the first web space of the hand, a second end of the strap fixable with the outside surface of the sheath proximate the palm;

whereby the strap and thumb retaining portion of the sheath together limiting a range of motion of the first metacarpal and stabilizing the CMC joint.

5. The sheath of claim 4 wherein the lacing arrangement includes one or more hook-and-loop fastener strips, a loop-side of each said one or more hook-and-loop fastener strips fixed with the sheath and a hook-side of each said the one or more hook-and-loop fastener strips removably fixable between two opposing lateral edges of the sheath.

6. The sheath of claim 4 wherein the lacing arrangement includes said one or more hook-and-loop fastener strips, a loop-side of each said one or more hook-and-loop fastener strips fixed with the sheath and a hook-side of each said one or more hook-and-loop fastener strips fixed with one or more cords of the at least one cord that are fixable between two opposing lateral edges of the sheath.

7. The sheath of claim 6 wherein each cord of said at least one cord is fixed with the two opposing lateral edges of the sheath at grommets disposed proximate each opposing lateral edge of the sheath of the two opposing lateral edges of the sheath.

8. The sheath of claim 4 wherein a flexible fabric web is disposed between each of two opposing lateral edges of the sheath.

9. The sheath of claim 4 wherein the sheath includes a moisture wicking spacer fabric material.

10. The sheath of claim 8 wherein the flexible fabric web includes a faux suede cloth material.

11. The sheath of claim 4 further including a first strap loop adapted to be positioned proximate a region corresponding to a palm when worn by a user and adapted to receive the strap therethrough.

12. The sheath of claim 4 further including a second strap loop adapted to be positioned proximate a region corresponding to a back of a hand when worn by a user and adapted to receive the strap therethrough.

13. The sheath of claim 4 further including a pocket fixed with the interior surface of the sheath and adapted to be positioned proximate a region corresponding to a first web space of the hand when worn by a user, the pocket adapted for receiving an insert that wraps around the first web space of the hand when the thumb brace is worn on the hand by the user, the insert further limiting a range of motion of the first metacarpal and stabilizing the CMC joint, the insert being a resilient or flexible elastomeric or plastic pad.

14. A sheath for securing about an appendage of a person, comprising:

a sheath having an outside surface, an interior surface, a front edge, a rear edge, a first lateral edge, and a second lateral edge; and a lacing arrangement comprising:

at least one pair of first lace apertures traversing the sheath proximate the first lateral edge of the sheath;

at least one pair of second lace apertures traversing the sheath proximate the second lateral edge of the sheath;

a pair of slits traversing the sheath proximate the first lateral edge and between each of the at least one pair of first lace apertures; and at least one cord having two opposing ends and threaded through one of the at least one pair of second lace apertures from the outside surface to the interior surface, around the first lateral edge of the sheath and through one of the at least one pair of first lace apertures from the outside surface to the interior surface, through one of the pair of slits from the interior surface to the outside surface, through an other of the pair of slits from the outside surface to the interior surface, through an other of the at least one pair of first lace apertures from the interior surface to the outside surface, around the first lateral edge of the sheath and back through an other of the at least one pair of second lace apertures, the two opposing ends of the at least one cord fixed together with one or more hook-and-loop fastener strips;

wherein the sheath is configured as a thumb brace adapted to be worn to partially encircle a back of a hand, a thumb, and a front portion of a palm of the hand, the sheath further including a thumb retaining portion having an open distal end adapted to receive the thumb therethrough, a flexible fabric web being disposed between each of two opposing lateral edges of the sheath, the sheath including a moisture wicking spacer fabric material;

a strap fixed at a first end with the interior surface of the sheath, traversing a strap aperture formed in the sheath, the strap being configured to extend over a first web space of the hand of a user when worn by the user, a second end of the strap fixable with the outside surface of the sheath proximate a palm of the hand when worn by the user; and a strap loop adapted to be positioned proximate a region corresponding to a back of a hand when worn by a user and adapted to receive the strap therethrough;

whereby the at least one cord may be pulled from the outside surface between the pair of slits to adjust a length of the at least one cord, the sheath secured about the person's hand, the one or more hook-and-loop fastener strips pulled tight and secured to the sheath with an attachment mechanism, the strap and thumb retaining portion of the sheath together limiting a range of motion of the first metacarpal and stabilizing the CMC joint.

\* \* \* \* \*